United States Patent
Sarvesh et al.

(10) Patent No.: US 10,836,776 B2
(45) Date of Patent: Nov. 17, 2020

(54) PROCESS FOR PREPARATION OF ERIBULIN AND INTERMEDIATES THEREOF

(71) Applicant: DR. REDDY'S LABORATORIES LIMITED, Hyderabad (IN)

(72) Inventors: Kumar Sarvesh, Secunderabad (IN); Debjit Basu, Hyderabad (IN); Raja gopal Penumandla, Warangal (IN); Prapulla Kumar Palvai, Nalgonda (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days.

(21) Appl. No.: 16/463,727

(22) PCT Filed: Nov. 23, 2017

(86) PCT No.: PCT/IB2017/057352
§ 371 (c)(1),
(2) Date: May 23, 2019

(87) PCT Pub. No.: WO2018/096478
PCT Pub. Date: May 31, 2018

(65) Prior Publication Data
US 2019/0276470 A1    Sep. 12, 2019

(30) Foreign Application Priority Data

Nov. 23, 2016  (IN) .............................. 201641039971
Jul. 10, 2017  (IN) .............................. 201741024255

(51) Int. Cl.
| | |
|---|---|
| C07D 493/22 | (2006.01) |
| C07D 307/26 | (2006.01) |
| C07D 407/12 | (2006.01) |
| C07D 407/14 | (2006.01) |
| C07F 7/00 | (2006.01) |
| C07D 493/04 | (2006.01) |
| C07D 307/12 | (2006.01) |
| C07F 7/18 | (2006.01) |

(52) U.S. Cl.
CPC ......... *C07D 493/22* (2013.01); *C07D 307/12* (2013.01); *C07D 307/26* (2013.01); *C07D 407/12* (2013.01); *C07D 407/14* (2013.01); *C07D 493/04* (2013.01); *C07F 7/00* (2013.01); *C07F 7/1804* (2013.01)

(58) Field of Classification Search
CPC .................................................. C07D 493/22
USPC ....................................................... 549/476
See application file for complete search history.

(56) References Cited

U.S. PATENT DOCUMENTS

| | | |
|---|---|---|
| 6,214,865 B1 | 4/2001 | Littlefield et al. |
| 6,469,182 B1 | 10/2002 | Littlefield et al. |
| 8,445,701 B2 | 5/2013 | Austad et al. |

FOREIGN PATENT DOCUMENTS

| | | |
|---|---|---|
| CN | 105713031 A | 6/2016 |
| IN | 3529/CHE/2013 A | 2/2015 |
| WO | 2005/118565 A1 | 12/2005 |
| WO | 2013/142999 A1 | 10/2013 |
| WO | 2017/064627 A2 | 4/2017 |
| WO | 2017/203459 A1 | 11/2017 |

OTHER PUBLICATIONS

Aicher, Thomas, Synthesis of Halichondrin B Norhalichondrin B, Harvard University, Cambridge MA J. Am. Chem. Soc. 1992, 114, pp. 3162-3164.
Bonini, Carlo, New Functionalized Hydroxymethyl Ketones from the Mild and Chemoselective KMnO4 Oxidation of Chiral Terminal Olefins., Eur.J. Org. Chem., 2006 pp. 80-83.
Habrant, Damien, Conversion of Carbonyl Compounds to Alkynes: General Overview and Recent Developments, Chem. Soc. Rev., 2010, 39, 2007-2017, Mar. 24, 2010.
Jiang, et al., A Novel Route to the F-Ring of Halichondrin B Diastereoselection in Pd(0)-Mediated Meso and C2 Diol Desymmetrization, Organic Letters, 2002 vol. 4, No. 20, 3411-3414.
Yu, Melvin, et al., From Micrograms to Grams: Scale-Up Synthesis of Eribulin Mesylate, Nat. Prod. Rep., 2013, 30, 1158-1164, Jul. 30, 2013.
Non-final office action dated Nov. 27, 2019 for U.S. Appl. No. 16/304,470.
Martin, MJ., et al. "Stellatolides, A New Cyclodepsipdptide Family from the Sponge Ecionemia Acervus: Isolation, Solid-Phase Total Synthesis, and Full Structural Assignment of Stellatolide A." J. Am. Chem. Soc. (2014), vol. 136, pp. 6754-6762.
International Search Report dated Sep. 19, 2017, for U.S. Appl. No. 16/304,470.
Written Opinion dated Sep. 19, 2017, for U.S. Appl. No. 16/304,470.
International Preliminary Report on Patentability dated Nov. 27, 2018, for U.S. Appl. No. 16/304,470.
International Search Report dated May 31, 2018, for corresponding International Patent Application No. PCT/IB2017/057352.
Written Opinion dated May 31, 2018, for corresponding International Patent Application No. PCT/IB2017/057352.
International Preliminary Report on Patentability dated May 28, 2019, for corresponding International Patent Application No. PCT/IB2017/057352.
Herbert C. Brown et. al., "Asymmetric Reduction with Chiral Organoboranes Based on alpha-Pinene", Acc. Chem. Res., vol. 25, No. 1, 1992.

*Primary Examiner* — Taofiq A Solola
(74) *Attorney, Agent, or Firm* — Pergament & Cepeda LLP; Milagros A. Cepeda; Edward D. Pergament

(57) ABSTRACT

The present application relate to process for preparation of tetrahydrofuran compound of formula II, 4-Methylene tetrahydrofuran compound of formula V and tetrahydropyran compound of formula IX which are useful as intermediates for the preparation of halichondrin B analogues such as Eribulin or its pharmaceutically acceptable salts.

3 Claims, No Drawings

PROCESS FOR PREPARATION OF ERIBULIN AND INTERMEDIATES THEREOF

This application is a National Stage Application under 35 U.S.C. § 371 of PCT International Application No. PCT/IB2017/057352, filed Nov. 23, 2017, which takes priority from Indian Provisional Application Numbers IN 201641039971, filed Nov. 23, 2016; and IN 201741024255, filed Jul. 10, 2017, all of which are herein incorporated in their entireties.

INTRODUCTION

Aspects of the present application relate to process for preparation of tetrahydrofuran compound of formula II, 4-Methylene tetrahydrofuran compound of formula V and tetrahydropyran compound of formula IX which are useful as intermediates for the preparation of halichondrin B analogues such as Eribulin or its pharmaceutically acceptable salts.

The drug compound having the adopted name Eribulin, is a synthetic analogue of halichondrin B, and is represented by structure of formula I.

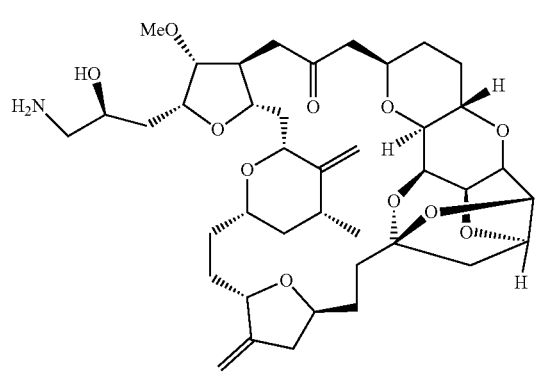

Eribulin is a microtubule inhibitor indicated for the treatment of patients with metastatic breast cancer who have previously received at least two chemotherapeutic regimens for the treatment of metastatic disease. U.S. Pat. No. 6,214,865 discloses eribulin and its pharmaceutically acceptable salts.

Process for the preparation of tetrahydrofuran compound of formula IIIa have been disclosed in PCT application No. WO 2005/118565 and Synlett 2013, vol. 24, pp. 327-332.

Process for the preparation of 4-Methylene tetrahydrofuran compound of formula V have been disclosed in PCT application No. 2005/118565A1, 2017/064627 A2, J. Am. Chem. Soc., 1992, 114, 3162 and Org. Lett., 2002, 4, 3411-3414.

The reported processes suffer from major disadvantages, including low yield, low diastereoselectivity and cumbersome crystallization procedures to improve the purity. Hence, there remains a need to provide an efficient processes for the preparation of tetrahydrofuran compound of formula II, 4-Methylene tetrahydrofuran compound of formula V and tetrahydropyran compound of formula IX which are simple, economic and industrially viable.

SUMMARY

In the first embodiment, the present application provides a process for preparation of tetrahydrofuran compound of formula II,

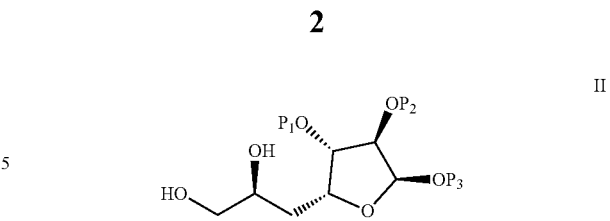

wherein $P_1$, $P_2$ and $P_3$ are same or different alcohol protecting groups; which includes one or more of the following steps:
(a) converting the compound of formula III to compound of formula IV, and

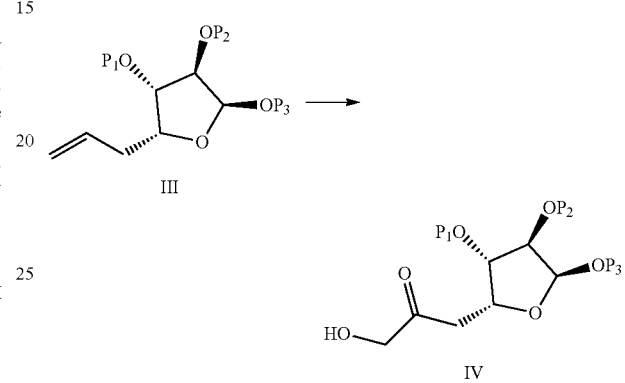

wherein $P_1$, $P_2$ and $P_3$ is independently hydrogen or an alcohol protecting group;
(b) reducing the keto group of formula IV using suitable catalyst to provide compound of formula II.

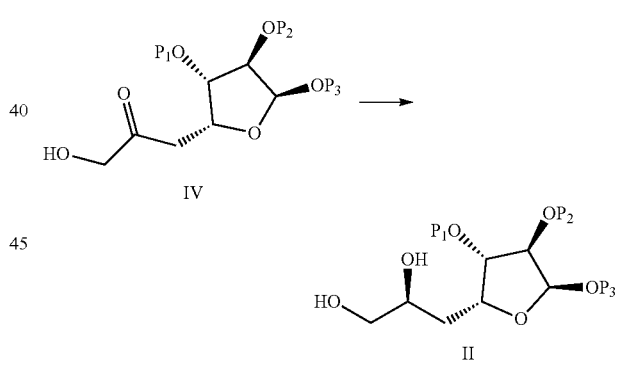

wherein $P_1$, $P_2$ and $P_3$ are defined above;

In the second embodiment, the present application provides a process for preparation of tetrahydrofuran compound of formula IIa,

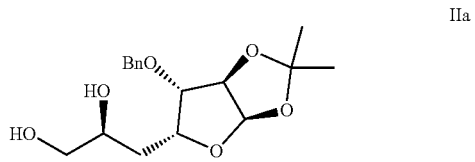 [SMILES: CC1(C)O[C@H]2O[C@H](C[C@H](O)CO)[C@H](OCc3ccccc3)[C@H]2O1]

which includes one or more of the following steps:
(a) converting the compound of formula IIIa to compound of formula IVa, and

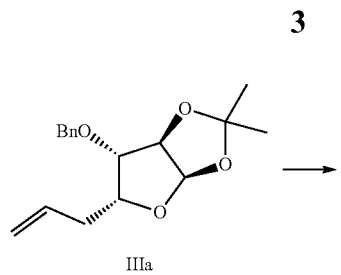

IIIa

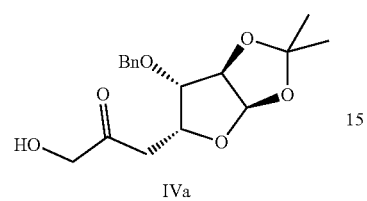

IVa (b) reducing the keto group of formula IVa using suitable catalyst to provide compound of formula IIa.

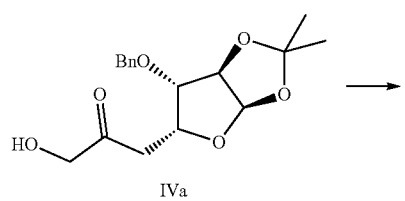

IVa

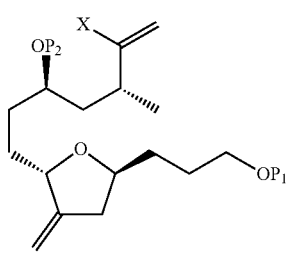

IIa

In the third embodiment, the present application provides a process for preparation of 4-Methylene tetrahydrofuran compound of formula V,

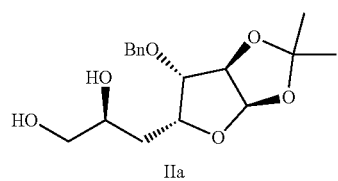

V wherein $P_1$ is H or an alcohol protecting group; $P_2$ is H or an alcohol protecting group or —$SO_2(R_1)$; wherein $R_1$ is selected from straight or branched $C_1$-$C_{10}$ alkyl or optionally substituted $C_5$-$C_{12}$ aryl; X is halogen; which includes one or more of the following steps:

(a) converting compound of formula VI to compound of formula VII;

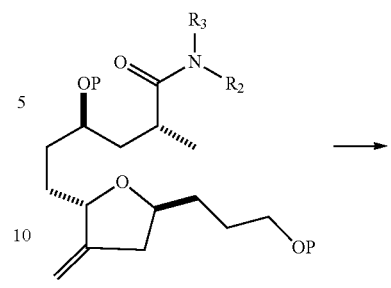

VI

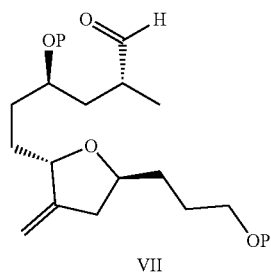

VII wherein P is an alcohol-protecting group; $R_2$, $R_3$ is same or different and are independently selected from hydrogen, alkyl, alkenyl, alkoxy, heteroalkyl, aryl, aralkyl, heteroaryl; all optionally substituted through available carbon atoms with 1, 2, 3, 4 or 5 groups selected from hydrogen, halo, alkyl, alkoxy, haloalkoxy, alkenyl, alkynyl, cycloalkyl, heteroalkyl, aryl, nitro, cyano, amino or substituted amino and the like or $R_2$ and $R_3$ together to form a 4-7 membered ring containing a 1-3 heteroatoms selected from N, O, S wherein one or more carbon or hetero atoms of the 4-7 membered ring optionally substituted with halo, alkyl, alkoxy, carbonyl, thiocarbonyl, haloalkoxy, alkenyl, alkynyl, cycloalkyl, heteroalkyl, aryl, nitro, cyano or amino; provided that when $R_2$ is methyl, then $R_3$ is not methoxy or when $R_3$ is methyl, then $R_2$ is not methoxy. For example, —$NR_2R_3$ include;

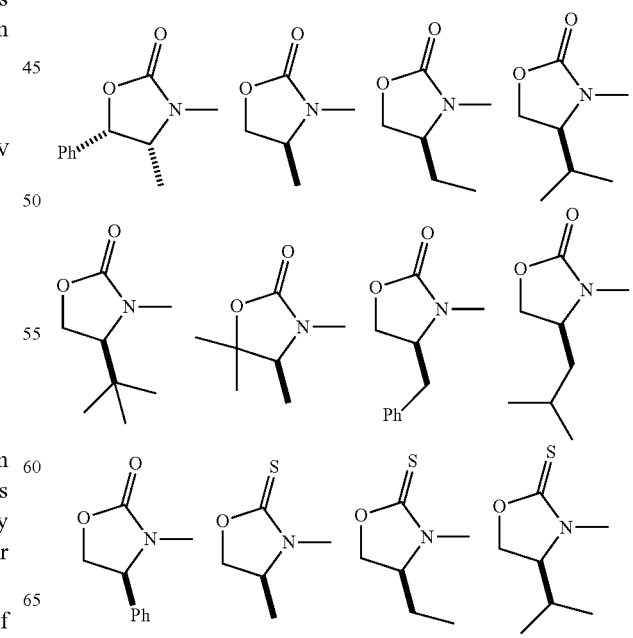

-continued

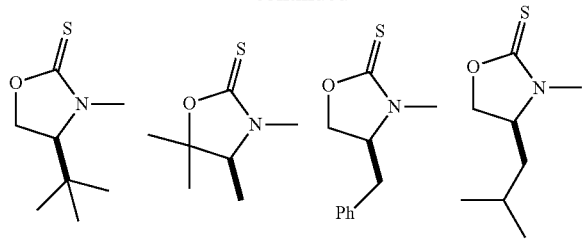

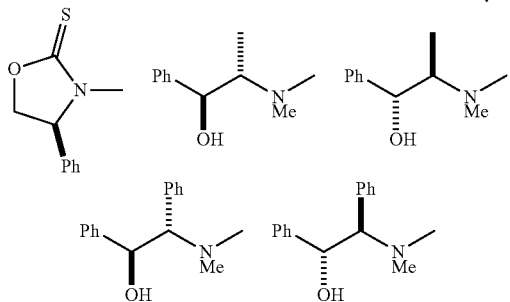

or stereoisomers thereof;
(b) converting compound of formula VII to compound of formula VIII; and

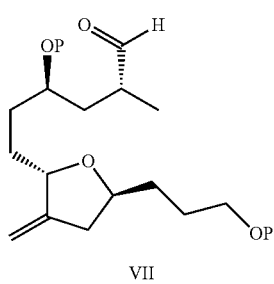
VII

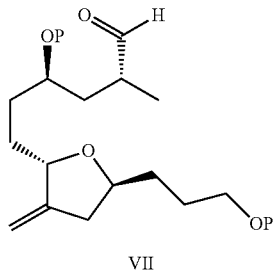
VIII (c) converting compound of formula VIII to compound of formula V.

In the fourth embodiment, the present application provides a process for preparation of 4-Methylene tetrahydrofuran compound of formula V,

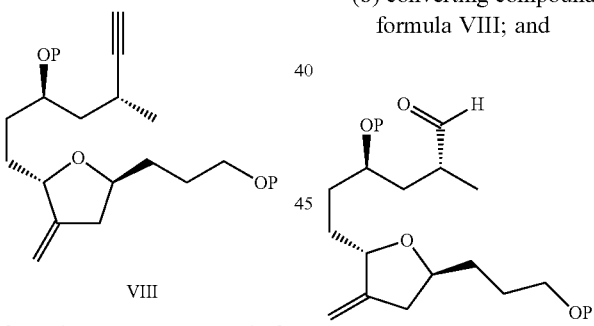
V wherein $P_1$ is H or an alcohol protecting group; $P_2$ is H or an alcohol protecting group or —$SO_2(R_1)$; wherein $R_1$ is selected from straight or branched $C_1$-$C_{10}$ alkyl or optionally substituted $C_5$-$C_{12}$ aryl; X is halogen;

which includes one or more of the following steps:
(a) converting compound of formula VIa to compound of formula VII;

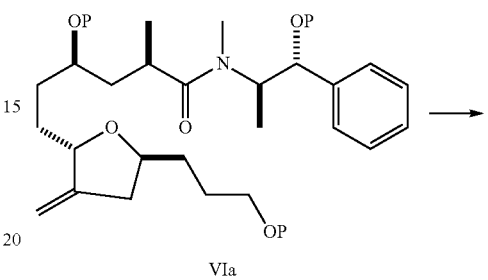
VIa

VII wherein P is an alcohol protecting group;
(b) converting compound of formula VII to compound of formula VIII; and

VII

VIII (c) converting compound of formula VIII to compound of formula V.

In the fifth embodiment, the present application provides a process for preparation of tetrahydropyran compound of formula IX,

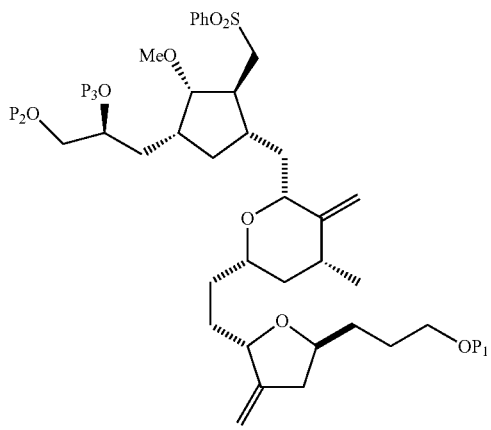

wherein $P_1$, $P_2$ and $P_3$ is an alcohol protecting group; which includes one or more of the following steps:
(a) reacting compound of formula Va with compound of formula X to provide compound of formula XI;

wherein $P_1$, $P_2$ and $P_3$ is an alcohol protecting group; X is a halogen selected from Cl, Br or I;
(b) converting compound of formula XI to compound of formula IX;

In the sixth embodiment, the present application provides a compound of formula Va or compound of formula Vb or compound of formula VII or compound of formula XI or compound of formula XIa or stereoisomers thereof.

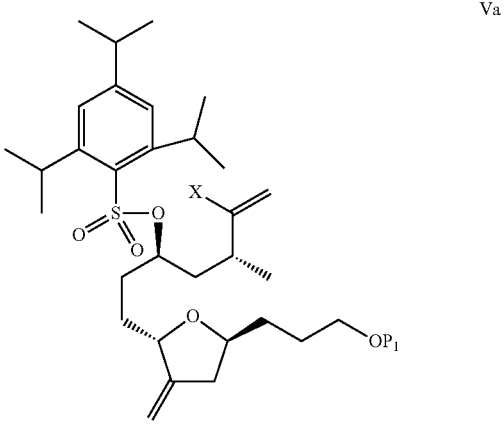

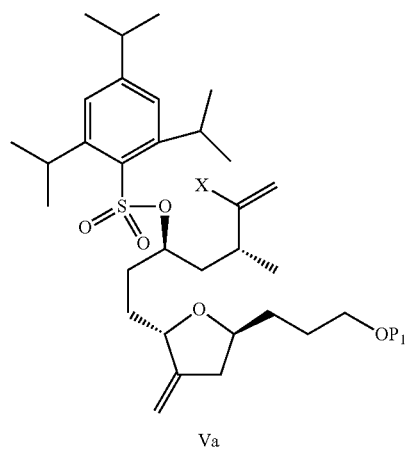

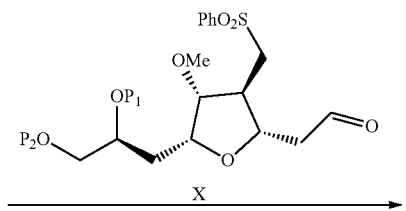

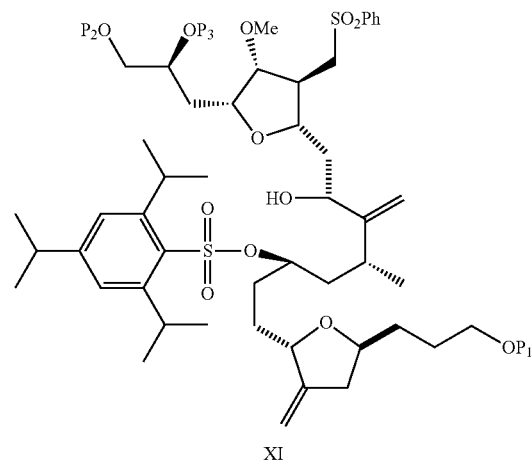

-continued

Vb
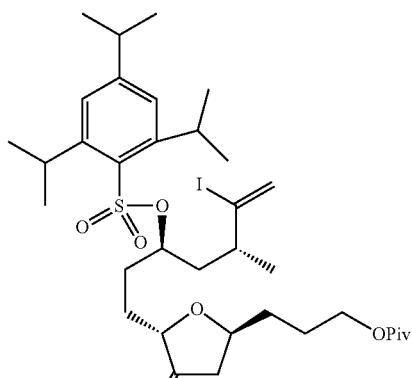

VII
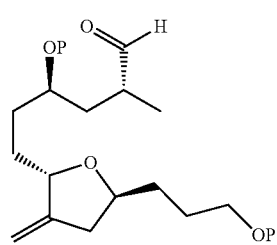

XI
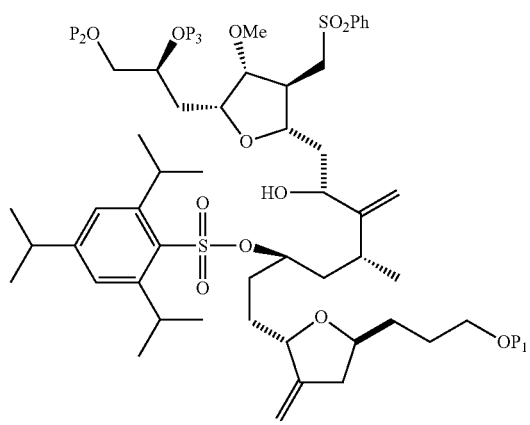

XIa
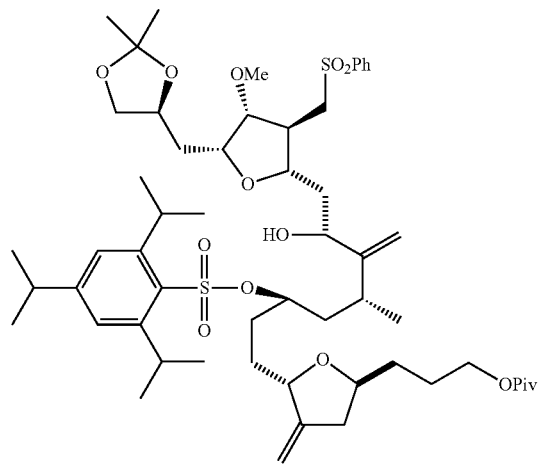

wherein P, P$_1$, P$_2$ and P$_3$ is same or different alcohol protecting group; X is a halogen selected from Cl, Br or I;

In the seventh embodiment, the present application provides a process for preparation of eribulin or a pharmaceutically acceptable salt thereof comprising synthesizing eribulin or its pharmaceutically acceptable salt from one or more compounds of formula Va, compound of formula Vb, compound of formula VII, compound of formula XI or compound of formula XIa or stereoisomers thereof.

DETAILED DESCRIPTION

In the first embodiment, the present application provides a process for preparation of tetrahydrofuran compound of formula II,

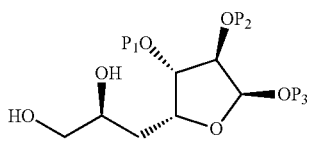

II wherein P$_1$, P$_2$ and P$_3$ is independently hydrogen or an alcohol protecting group; which includes one or more of the following steps:
(a) converting the compound of formula III to compound of formula IV, and

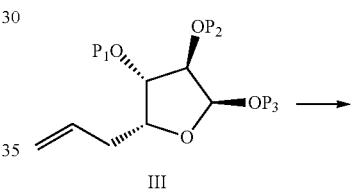

III

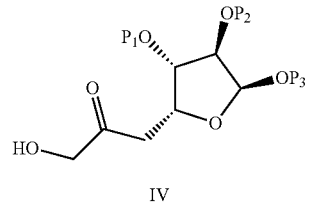

IV wherein P$_1$, P$_2$ and P$_3$ is independently hydrogen or an alcohol protecting group;
(b) reducing the keto group of formula IV using suitable catalyst to provide compound of formula II.

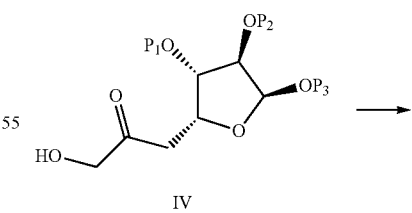

IV

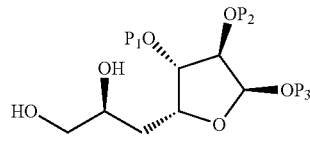

II wherein P$_1$, P$_2$ and P$_3$ are defined above;

Step (a) involves converting the compound of formula III to compound of formula IV;

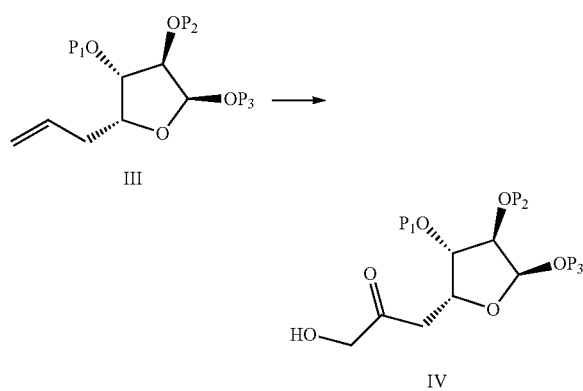

wherein $P_1$, $P_2$ and $P_3$ is independently hydrogen or an alcohol protecting group;

Suitable reagents that may be used in step (a) include potassium permanganate and the like or any other oxidizing agent that are known in the art.

Step (a) may be carried out in acidic conditions or in basic conditions or combination thereof. Suitable acids that may be used in step (a) include acetic acid, formic acid, propanoic acid, butyric acid, oxalic acid and the like or mixtures thereof. Suitable bases that may be used in step (a) include sodium bicarbonate, potassium bicarbonate, sodium carbonate, potassium carbonate and the like or mixtures thereof.

Suitable solvents that may be used in step (a) include water, ethers, ketones, aliphatic and alicyclic hydrocarbons, aromatic hydrocarbons, halogenated hydrocarbon, nitriles, polar aprotic solvents or mixtures thereof.

The reaction mixture obtained from step (a) may be optionally processed to remove any insoluble solids, and particles may be removed by methods such as decantation, centrifugation, gravity filtration, suction filtration, or any other techniques for the removal of solids. The product of step (a) may be isolated directly from the reaction mixture itself after the reaction is complete in step (a), or after conventional work up with techniques such as filtration, quenching with a suitable reagent, extraction, or the like. Optionally, the resulting product may be directly used for step (b) with or without isolation or it may be further purified.

Step (b) involves reducing the keto group of formula IV using suitable catalyst to provide compound of formula II.

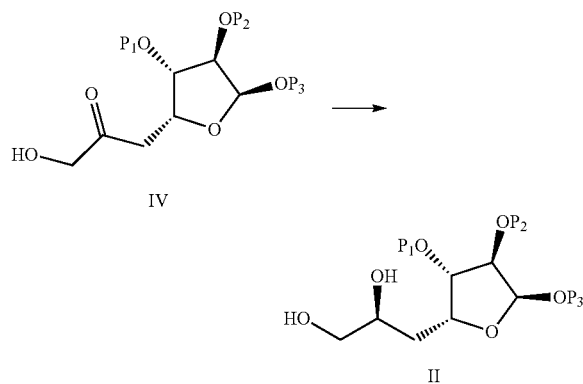

wherein $P_1$, $P_2$ and $P_3$ are defined above;

Suitable reagents that may be used in step (b) include, sodium borohydride, lithium aluminum hydride, sodium trimethoxy borohydride, Lithium borohydride, acetoxyborohydride, cyanoborohydride, sodium dihydro-bis-(2-methoxyethoxy) aluminate solution (VITRIDE®), (+)-B-Chlorodiisopinocampheylborane, (S)-(−)-2-Methyl-CBS-oxazaborolidine, diisobutyl aluminium hydride, 9-borabicyclo(3.3.1)nonane (9-BBN), catecholborane, pinacolborane, cyclohexylborane or any other suitable reductants known in the art. Suitable enzymes that may be used in step (b) include keto reductase such as KRED-P1-001, KRED-P1-H10, KRED-P2-D11 and KRED-101 from Codexis®; ProAKR007 and ProAKR045 from Prozomix; KRED-EW-N122 and KRED-EW-N124 from Enzymeworks; CRED A231 and CRED A631 from Almac; and the like or any other suitable enzyme known in the art.

Suitable solvents that may be used in step (b) include water, alcohols, ethers, aliphatic and alicyclic hydrocarbons, halogenated hydrocarbons, aromatic hydrocarbons or any mixtures of two or more thereof.

The reaction mixture obtained from step (b) may be optionally processed to remove any insoluble solids, and particles may be removed by methods such as decantation, centrifugation, gravity filtration, suction filtration, or any other techniques for the removal of solids. The product of step (b) may be isolated directly from the reaction mixture itself after the reaction is complete in step (b), or after conventional work up with techniques such as filtration, quenching with a suitable reagent, extraction, or the like. Optionally, the resulting product may be directly used for next step with or without isolation or it may be further purified, if isolated.

An aspect of the first embodiment further comprises converting the compound of Formula II obtained therein to eribulin or a pharmaceutically acceptable salt thereof.

Said conversion of compound formula II to eribulin or a pharmaceutically acceptable salt thereof may be carried out by a suitable process known in the art.

In the second embodiment, the present application provides a process for preparation of tetrahydrofuran compound of formula IIa,

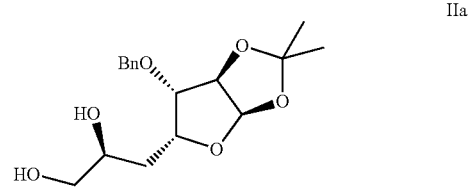 [SMILES: CC1(C)O[C@H]2O[C@H](C[C@H](O)CO)[C@H](OCc3ccccc3)[C@H]2O1]

which includes one or more of the following steps:
(a) converting the compound of formula IIIa to compound of formula IVa, and

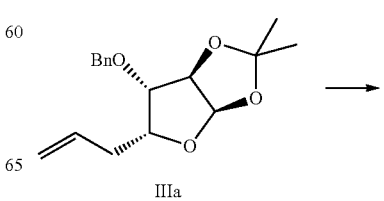

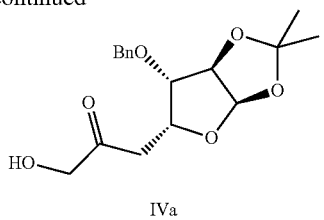

IVa (b) reducing the keto group of formula IVa using suitable catalyst to provide compound of formula IIa.

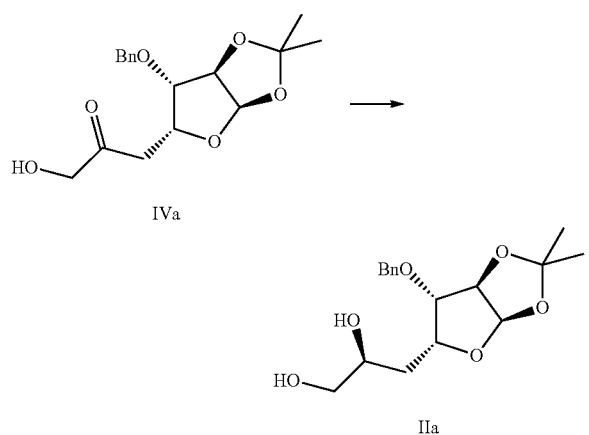

Step (a) involves converting the compound of formula IIIa to compound of formula IVa.

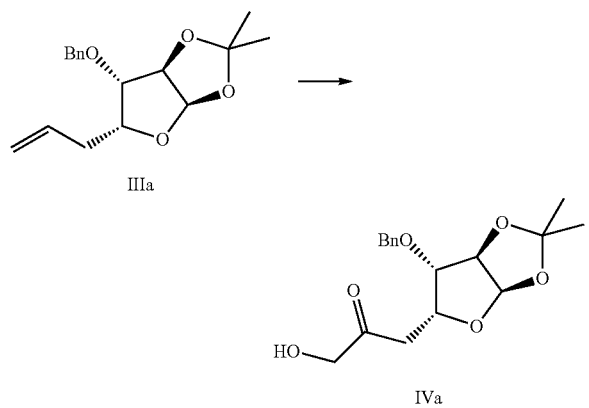

Suitable reagents that may be used in step (a) include potassium permanganate and the like or any other oxidizing agent that are known in the art. Step (a) may be carried out in acidic conditions or in basic conditions or combination thereof. Suitable acids that may be used in step (a) include acetic acid, formic acid, propanoic acid, butyric acid, oxalic acid and the like or mixtures thereof. Suitable bases that may be used in step (a) include sodium bicarbonate, potassium bicarbonate, sodium carbonate, potassium carbonate and the like or mixtures thereof.

Suitable solvents that may be used in step (a) include water, ethers, ketones, aliphatic and alicyclic hydrocarbons, aromatic hydrocarbons, halogenated hydrocarbon, nitriles, polar aprotic solvents or mixtures thereof.

The reaction mixture obtained from step (a) may be optionally processed to remove any insoluble solids, and particles may be removed by methods such as decantation, centrifugation, gravity filtration, suction filtration, or any other techniques for the removal of solids. The product of step (a) may be isolated directly from the reaction mixture itself after the reaction is complete in step (a), or after conventional work up with techniques such as filtration, quenching with a suitable reagent, extraction, or the like. Optionally, the resulting product may be directly used for step (b) with or without isolation or it may be further purified.

Step (b) involves reducing the keto group of formula IVa using suitable catalyst to provide compound of formula IIa.

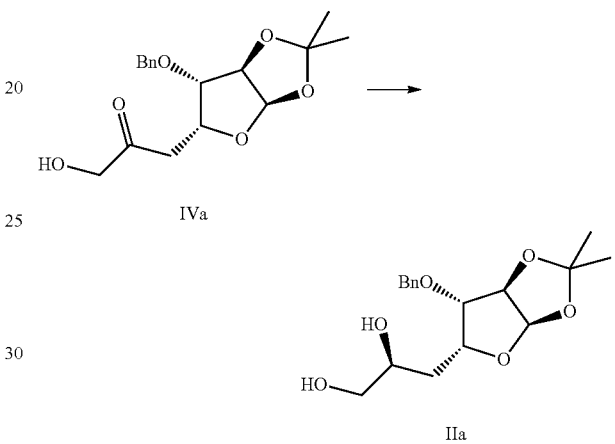

Suitable reagents that may be used in step (b) include, sodium borohydride, lithium aluminum hydride, sodium trimethoxy borohydride, Lithium borohydride, acetoxyborohydride, cyanoborohydride, sodium dihydro-bis-(2-methoxyethoxy) aluminate solution (VITRIDE®), (+)-B-Chlorodiisopinocampheylborane, (S)-(−)-2-Methyl-CBS-oxazaborolidine, diisobutyl aluminium hydride, 9-borabicyclo(3.3.1)nonane (9-BBN), catecholborane, pinacolborane, cyclohexylborane or any other suitable reductants known in the art. Suitable enzymes that may be used in step (b) include keto reductase such as KRED-P1-001, KRED-P1-H10, KRED-P2-D11 and KRED-101 from Codexis®; ProAKR007 and ProAKR045 from Prozomix; KRED-EW-N122 and KRED-EW-N124 from Enzymeworks; CRED A231 and CRED A631 from Almac; and the like or any other suitable enzyme known in the art.

Suitable solvents that may be used in step (b) include water, alcohols, ethers, aliphatic and alicyclic hydrocarbons, halogenated hydrocarbons, aromatic hydrocarbons or any mixtures of two or more thereof.

The reaction mixture obtained from step (b) may be optionally processed to remove any insoluble solids, and particles may be removed by methods such as decantation, centrifugation, gravity filtration, suction filtration, or any other techniques for the removal of solids. The product of step (b) may be isolated directly from the reaction mixture itself after the reaction is complete in step (b), or after conventional work up with techniques such as filtration, quenching with a suitable reagent, extraction, or the like. Optionally, the resulting product may be directly used for next step with or without isolation or it may be further purified, if isolated.

An aspect of the second embodiment further comprises converting the compound of Formula IIa obtained therein to eribulin or a pharmaceutically acceptable salt thereof.

Said conversion of compound formula IIa to eribulin or a pharmaceutically acceptable salt thereof may be carried out by a suitable process known in the art.

In the third embodiment, the present application provides a process for preparation of 4-Methylene tetrahydrofuran compound of formula V,

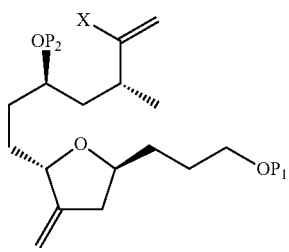

V wherein $P_1$ is H or an alcohol protecting group; $P_2$ is H or an alcohol protecting group or —$SO_2(R_1)$; wherein $R_1$ is selected from straight or branched $C_1$-$C_{10}$ alkyl or optionally substituted $C_5$-$C_{12}$ aryl; X is halogen;
which includes one or more of the following steps:
(a) converting compound of formula VI to compound of formula VII;

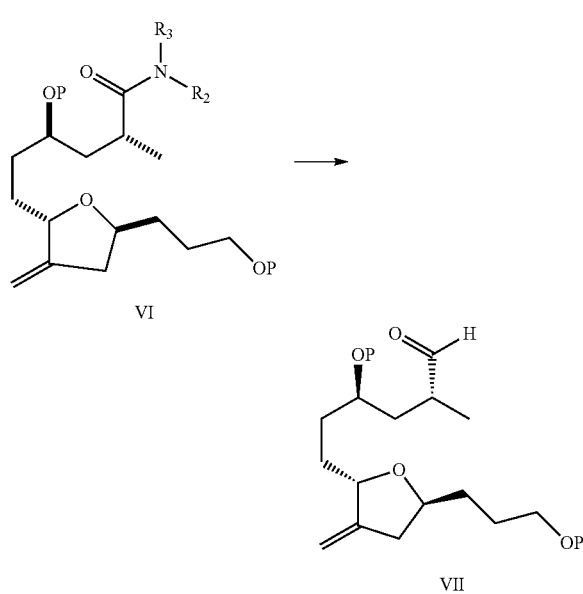

wherein P is an alcohol-protecting group; $R_2$, $R_3$ is same or different and are independently selected from hydrogen, alkyl, alkenyl, alkoxy, heteroalkyl, aryl, aralkyl, heteroaryl; all optionally substituted through available carbon atoms with 1, 2, 3, 4 or 5 groups selected from hydrogen, halo, alkyl, alkoxy, haloalkoxy, alkenyl, alkynyl, cycloalkyl, heteroalkyl, aryl, nitro, cyano, amino or substituted amino and the like or $R_2$ and $R_3$ together to form a 4-7 membered ring containing a 1-3 heteroatoms selected from N, O, S wherein one or more carbon or hetero atoms of the 4-7 membered ring optionally substituted with halo, alkyl, alkoxy, carbonyl, thiocarbonyl, haloalkoxy, alkenyl, alkynyl, cycloalkyl, heteroalkyl, aryl, nitro, cyano or amino; provided that when $R_2$ is methyl, then $R_3$ is not methoxy or when $R_3$ is methyl, then $R_2$ is not methoxy. For example, —$NR_2 R_3$ include;

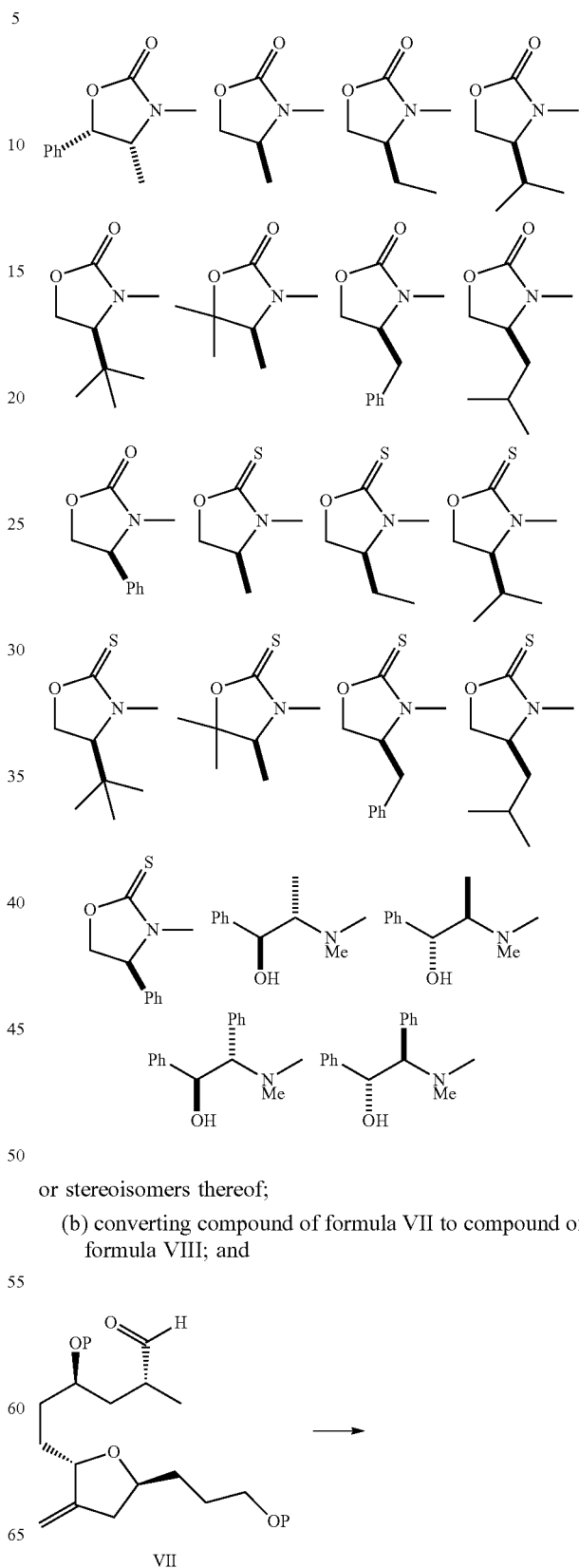

or stereoisomers thereof;
(b) converting compound of formula VII to compound of formula VIII; and

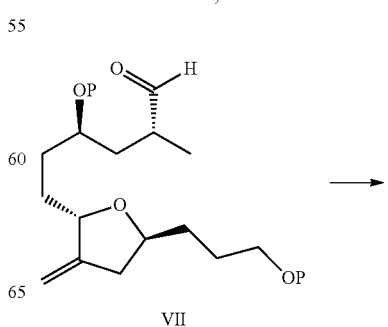

VII

-continued

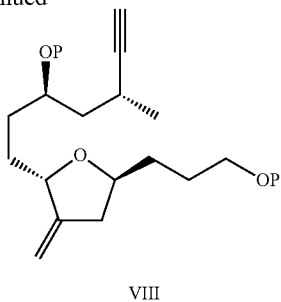

VIII (c) converting compound of formula VIII to compound of formula V.

Step (a) involves converting compound of formula VI to compound of formula VII;

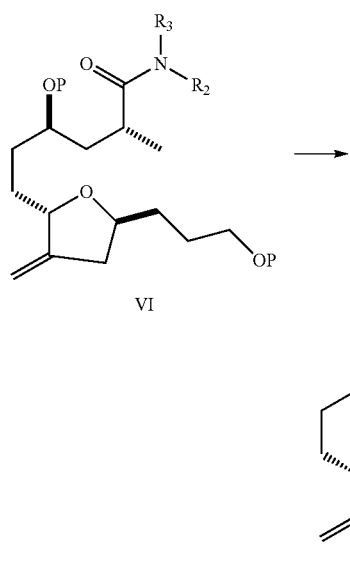

VI

VII

Compound of formula VI is prepared by following the procedure disclosed in our co-pending PCT application No. PCT/IB2017/053082.

Step(a) may be directly converted compound of formula VI to compound of formula VII or may be carried out in two steps. The first step involves reduction of compound of formula VI to provide corresponding alcohol compound of the formula VI and the second step involves the oxidation of alcohol compound to aldehyde compound of formula VII.

Suitable reagents that may be used in step (a) for reduction of compound of formula VI include n-Butyllithium, lithium tri(ethoxy)aluminium hydride, diisobutylaluminium hydride, disiamylborane lithium bis(trimethylsilyl)amide, lithium diisopropylamide and the like or any other suitable reagents known in the art.

Suitable solvents that may be used in step (a) for reduction of compound of formula VI include ethers, aliphatic and alicyclic hydrocarbons, halogenated hydrocarbons or mixtures thereof.

Suitable reagents that may be used in step (a) for oxidation include Swern conditions, Dess Martin periodinane, TPAP/NMO, TEMPO/bis-acetoxyiodobenzene, chromium (VI) oxidants such as PDC, PCC and the like or any other suitable oxidizing reagents that are known in the art.

Suitable solvents that may be used in step (a) for oxidation include ethers, aliphatic and alicyclic hydrocarbons, halogenated hydrocarbons, polar aprotic solvents or mixtures thereof.

The reaction mixture obtained from step (a) may be optionally processed to remove any insoluble solids, and particles may be removed by methods such as decantation, centrifugation, gravity filtration, suction filtration, or any other techniques for the removal of solids. The product of step (a) may be isolated directly from the reaction mixture itself after the reaction is complete in step (a), or after conventional work up with techniques such as filtration, quenching with a suitable reagent, extraction, or the like. Optionally, the resulting product may be directly used for step (b) with or without isolation or it may be further purified.

Step (b) involves converting compound of formula VII to compound of formula VIII; and

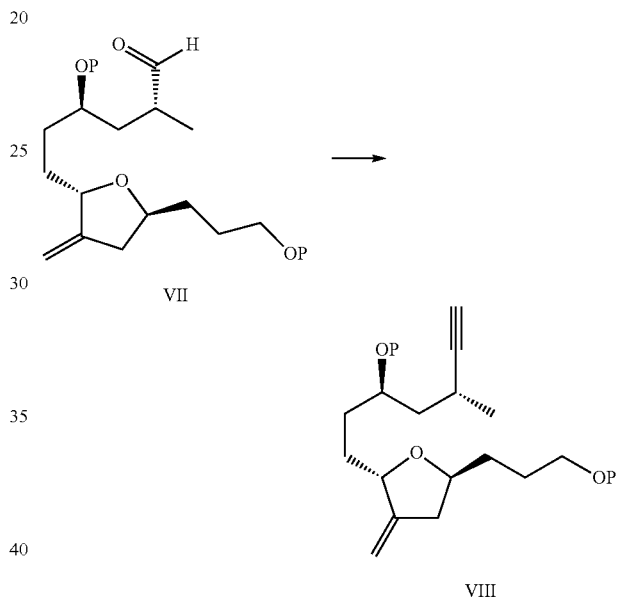

VII

VIII

Suitable reagents that may be used in step (b) include ethyl, iso-propyl, t-butyl phosphonate esters such as dimethyl (1-diazo-2-oxopropyl)phosphonate and the like, Suitable bases that may be used in step (b) include, alkali metal or alkaline earth metal hydroxides such as sodium hydroxide, potassium hydroxide, lithium hydroxide, calcium hydroxide; carbonates such as sodium carbonate, potassium carbonate, cesium carbonate, calcium carbonate, magnesium carbonate, sodium bicarbonate, potassium bicarbonate, alkoxides such as sodium methoxide, potassium methoxide; organic bases, such as for example, triethylamine, tributylamine, N-methylmorpholine, N,N-diisopropylethylamine, N-methylpyrrolidine, pyridine, collidine 4-(N, N-dimethylamino)pyridine, morpholine, imidazole, 2-methylimidazole, 4-methylimidazole and the like or any other suitable base known in the art.

Suitable solvents that may be used in step (b) include alcohols, halogenated hydrocarbons, nitriles, polar aprotic solvents, nitromethane or mixtures thereof.

The reaction mixture obtained from step (b) may be optionally processed to remove any insoluble solids, and particles may be removed by methods such as decantation, centrifugation, gravity filtration, suction filtration, or any other techniques for the removal of solids. The product of step (b) may be isolated directly from the reaction mixture itself after the reaction is complete in step (b), or after conventional work up with techniques such as filtration, quenching with a suitable reagent, extraction, or the like. Optionally, the resulting product may be directly used for step (c) with or without isolation or it may be further purified.

Step (c) involves converting compound of formula VIII to compound of formula V.

Conversion of compound of formula VIII to compound of formula V may be carried out using procedure disclosed in PCT publication No. WO 2017/064627A2.

Optionally steps (a) to (c) or any two or more steps may be carried out as in-situ i.e. without isolating the intermediates in each stage.

An aspect of the third embodiment further comprises converting the compound of Formula V obtained therein to eribulin or a pharmaceutically acceptable salt thereof.

Said conversion of compound formula V to eribulin or a pharmaceutically acceptable salt thereof may be carried out by a suitable process known in the art.

In the fourth embodiment, the present application provides a process for preparation of 4-Methylene tetrahydrofuran compound of formula V,

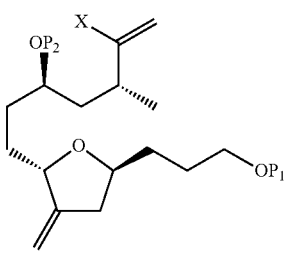

V wherein $P_1$ is H or an alcohol protecting group; $P_2$ is H or an alcohol protecting group or $-SO_2(R_1)$; wherein $R_1$ is selected from straight or branched $C_1$-$C_{10}$ alkyl or optionally substituted $C_5$-$C_{12}$ aryl; X is halogen;

which includes one or more of the following steps:
(a) converting compound of formula VIa to compound of formula VII;

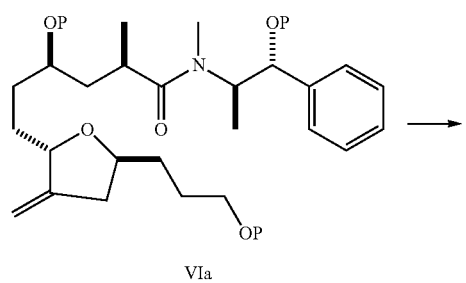

VIa

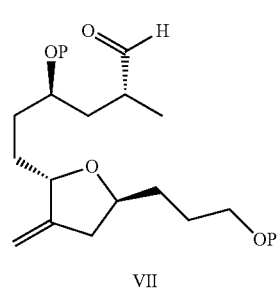

VII wherein P is an alcohol protecting group;

(b) converting compound of formula VII to compound of formula VIII; and

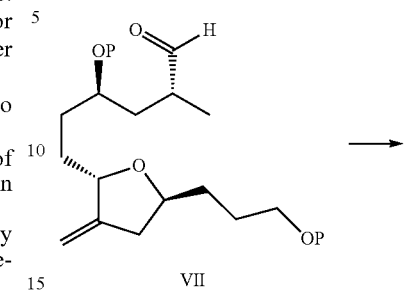

VII

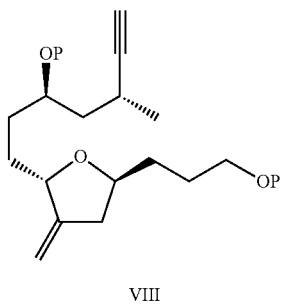

VIII (c) converting compound of formula VIII to compound of formula V.

In the fifth embodiment, the present application provides a process for preparation of tetrahydropyran compound of formula IX,

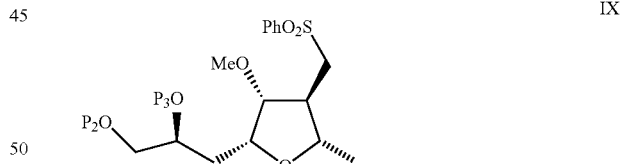

IX wherein $P_1$, $P_2$ and $P_3$ is an alcohol protecting group; which includes one or more of the following steps:

(a) reacting compound of formula Va with compound of formula X to provide compound of formula XI;

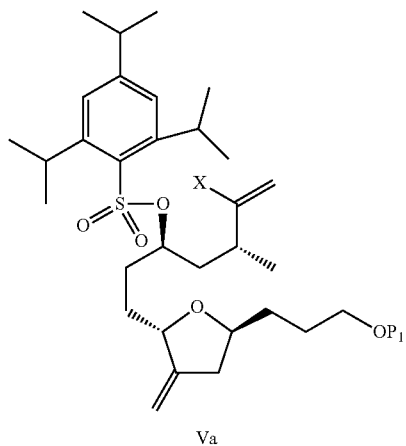
Va
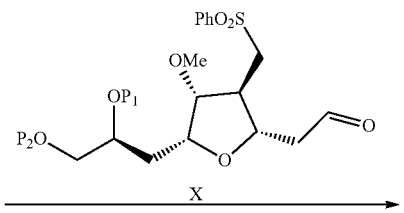
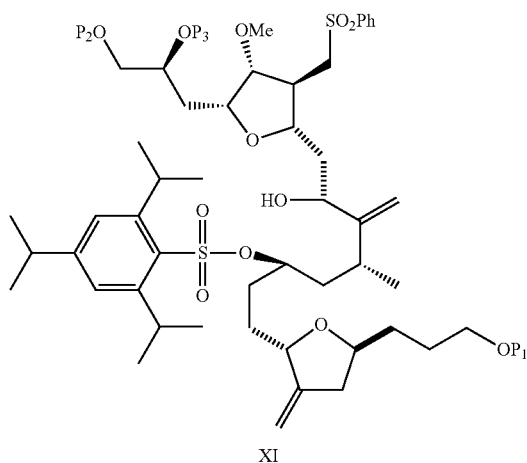
XI
wherein $P_1$, $P_2$ and $P_3$ is an alcohol protecting group; X is halogen selected from Cl, Br or I;
(b) converting compound of formula XI to compound of formula IX;
Step (a) involves reacting compound of formula Va with compound of formula X to provide compound of formula XI;
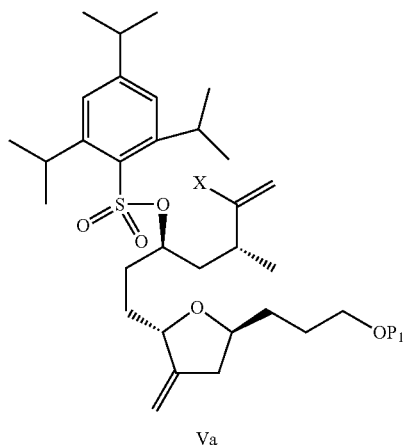
Va
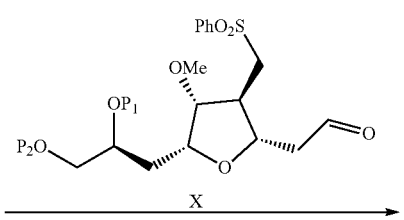

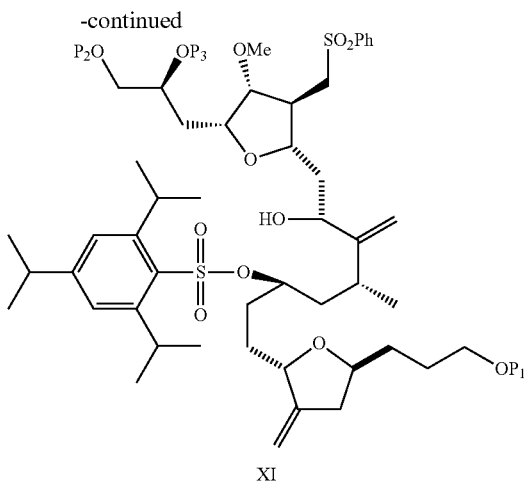

XI

Compound of formula Va prepared by treating corresponding alcohol compound of formula Vc with 2,4,6-triisopropylbenzene-1-sulfonyl chloride.

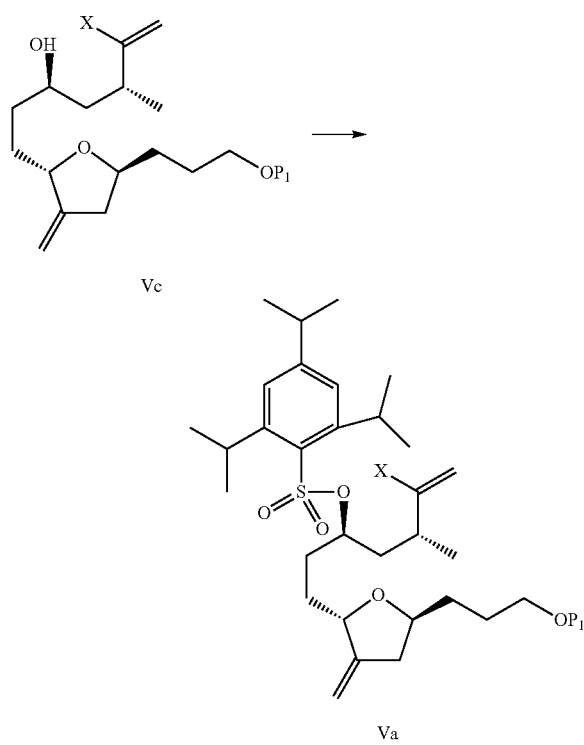

Various sulfonate derivatives of compounds of formula Vc including p-toluenesulfonate of formula Vc, p-nitrobenzenesulfonate of formula Vc, p-methoxybenzenesulfonate of formula Vc, 2,4,6-triisopropylbenzenesulfonate of formula Vc (formula Va) and the methane sulfonate of formula Vc were screened to arrive suitable sulfonate compound of formula Vc for synthesis of compound of formula IX. We discovered that 2,4,6-triisopropylbenzenesulfonate of formula Vc (formula Va) participated productively in NHK followed by cyclization reaction to provide desired compound of formula XI and subsequent cyclization reaction compound of formula IX with cleaner reaction profile. For example, compound of formula IX was prepared with diastereoselectivity of 14:1 starting with 2,4,6-triisopropylbenzenesulfonate of formula Vc (compound of formula Vb) whereas diastereoselectivity of compound of formula IX is 9:1 when the compound of formula IX was prepared starting from methane sulfonate derivative of compound of formula Vc.

Suitable reagents that may be used in step (a) include, chromium chloride and optionally a ligand such as (S)-N-(2-(4-isopropyl-4,5-dihydrooxazol-2-yl)-6-methylphenyl)methanesulfonamide and the like, nickel chloride and optionally a ligand such as 2,9-dimethyl-1,10-phenanthroline and the like or any other suitable catalyst or ligands known in the art used in Nozaki-Hiyama-Kishi (NHK) reaction.

Suitable bases that may be used in step (a) include, sodium hydride, potassium tert-butoxide, sodium methoxide, lithium hexamthyldisilazide, sodium amide, 1,8-bis(dimethylamino)naphthalene (Proton-sponge) and the like; other organic bases, such as for example, triethylamine, ethylenediamine, N-methylmorpholine, N-methylpyrrolidine, pyridine, 4-(N,N-dimethylamino)pyridine, morpholine, imidazole and the like or any other suitable base known in the art.

Suitable solvents that may be used in step (a) include, ethers, aliphatic and alicyclic hydrocarbons, aromatic hydrocarbons, nitriles, polar aprotic solvents or mixtures thereof.

The reaction mixture obtained from step (a) may be optionally processed to remove any insoluble solids, and particles may be removed by methods such as decantation, centrifugation, gravity filtration, suction filtration, or any other techniques for the removal of solids. The product of step (a) may be isolated directly from the reaction mixture itself after the reaction is complete in step (a), or after conventional work up with techniques such as filtration, quenching with a suitable reagent, extraction, or the like. Optionally, the resulting product may be directly used for step (b) with or without isolation or it may be further purified, if isolated, to improve the purity of the product.

Step (b) involves converting compound of formula XI to compound of formula IX;

Suitable reagents that may be used in step (b) include potassium bis(trimethylsilyl)amide (KHMDS) or any other suitable reducing agents known in the art.

Suitable solvents that may be used in step (b) include, ethers, aliphatic and alicyclic hydrocarbons, aromatic hydrocarbons, nitriles, polar aprotic solvents or mixtures thereof.

The reaction mixture obtained from step (b) may be optionally processed to remove any insoluble solids, and particles may be removed by methods such as decantation, centrifugation, gravity filtration, suction filtration, or any other techniques for the removal of solids. The product of step (b) may be isolated directly from the reaction mixture itself after the reaction is complete in step (b), or after conventional work up with techniques such as filtration, quenching with a suitable reagent, extraction, or the like. Optionally, the resulting product may be directly used for next step with or without isolation or it may be further purified, if isolated, to improve the purity of the product.

An aspect of the fifth embodiment further comprises converting the compound of Formula IX obtained therein to eribulin or a pharmaceutically acceptable salt thereof.

Said conversion of compound formula IX to eribulin or a pharmaceutically acceptable salt thereof may be carried out by a suitable process known in the art.

In the sixth embodiment, the present application provides a compound of formula Va or compound of formula Vb or compound of formula VII or compound of formula XI or compound of formula XIa or stereoisomers thereof.

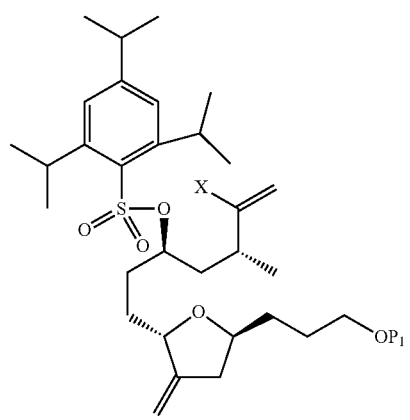

Va

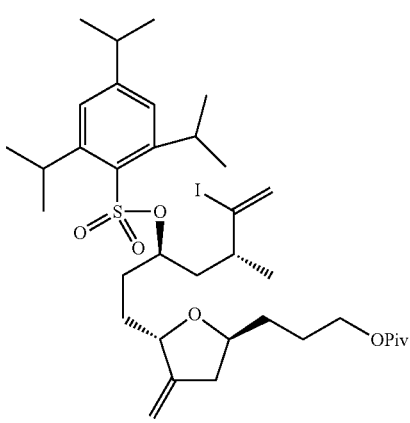

Vb

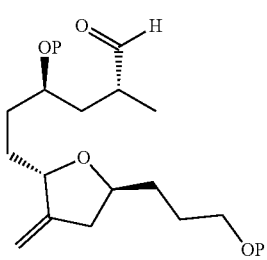

VII

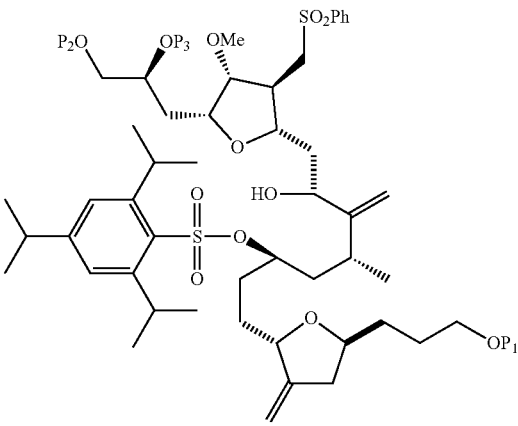

XI

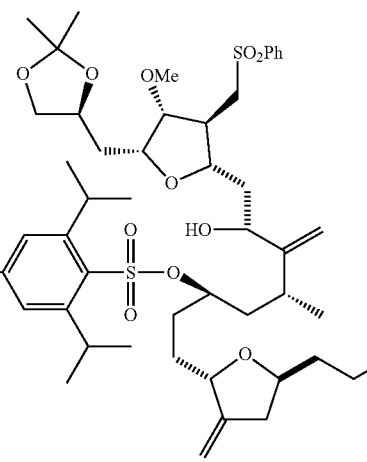

XIa wherein P, $P_1$, $P_2$ and $P_3$ is same or different alcohol protecting group; X is halogen selected from Cl, Br or I;

In the seventh embodiment, the present application provides a process for preparation of eribulin or a pharmaceutically acceptable salt thereof comprising synthesizing eribulin or its pharmaceutically acceptable salt from one or more compounds of formula Va, compound of formula Vb, compound of formula VII, compound of formula XI or compound of formula XIa or stereoisomers thereof.

Definitions

The following definitions are used in connection with the present application unless the context indicates otherwise. In general, the number of carbon atoms present in a given group or compound is designated "$C_x$-$C_y$", where x and y are the lower and upper limits, respectively. For example, a group designated as "$C_1$-$C_6$" contains from 1 to 6 carbon atoms. The carbon number as used in the definitions herein refers to carbon backbone and carbon branching, but does not include carbon atoms of the substituents, such as alkoxy substitutions or the like.

As used herein, "an alcohol protecting group" is a functional group that protects the alcohol group from participating in reactions that are occurring in other parts of the molecule. Suitable alcohol protecting groups that are used in the present application include, two alcohol groups together protected by forming acetonide (cyclic ketal), acetyl, benzoyl, benzyl, β-methoxyethoxymethyl ether, methoxymethyl ether, dimethoxytrityl, p-methoxybenzyl ether, methylthiomethyl ether, allyl ether, t-butyl ether, pivaloyl, trityl, silyl ether (e.g., trimethylsilyl (TMS), t-butyldimethylsilyl (TBMDS), t-butyldiphenylsilyl (TBDPS), t-butyldimethylsilyloxymethyl (TOM) or triisopropylsilyl (TIPS) ether), tetrahydropyranyl (THP), methyl ether and ethoxyethyl ether (EE) or any suitable alcohol protecting group known in the art used for protecting alcohols.

As used herein, the term "lower alkyl", "alkyl" or "alk" includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof.

As used herein, the term "lower alkenyl" or "alkenyl" as used by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

As used herein, the term "halogen" or "halo" as used herein alone or as part of another group refers to chlorine, bromine, fluorine, and iodine.

As used herein, the term "aryl" as alone or as part of another group refers to monocyclic and bicyclic aromatic groups containing 6 to 10 carbons in the ring portion such as phenyl or naphthyl including 1-naphthyl and 2-naphthyl and the like.

As used herein, the term "lower alkoxy", "alkoxy", "aryloxy" or "aralkoxy" as alone or as part of another group includes any of the above alkyl, aralkyl or aryl groups linked to an oxygen atom.

As used herein, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides.

An "alcohol" is an organic compound containing a carbon bound to a hydroxyl group. "$C_1$-$C_6$ alcohols" include methanol, ethanol, 2-nitroethanol, 2-fluoroethanol, 2,2,2-trifluoroethanol, hexafluoroisopropyl alcohol, ethylene glycol, 1-propanol, 2-propanol (isopropyl alcohol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, cyclohexanol, diethylene glycol monomethyl ether, diethylene glycol monoethyl ether, cyclohexanol, phenol, glycerol, 2-methoxyethanol, 2-ethoxyethanol and the like.

An "aliphatic hydrocarbon" is a liquid hydrocarbon compound, which may be linear, branched, or cyclic and may be saturated or have as many as two double bonds. A liquid hydrocarbon compound that contains a six-carbon group having three double bonds in a ring is called "aromatic." Examples of "$C_5$-$C_8$ aliphatic or aromatic hydrocarbons" include n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, petroleum ethers and the like.

An "aromatic hydrocarbon solvent" refers to a liquid, unsaturated, cyclic, hydrocarbon containing one or more rings which has delocalized conjugated π system. Examples of an aromatic hydrocarbon solvent include benzene toluene, ethylbenzene, m-xylene, o-xylene, p-xylene, indane, naphthalene, tetralin, trimethylbenzene, chlorobenzene, fluorobenzene, trifluorotoluene, anisole, $C_6$-$C_{12}$ aromatic hydrocarbons and the like.

An "ester" is an organic compound containing a carboxyl group —(C═O)—O— bonded to two other carbon atoms. "$C_3$-$C_6$ esters" include ethyl acetate, n-propyl acetate, n-butyl acetate, isobutyl acetate, t-butyl acetate, ethyl formate, methyl acetate, methyl propanoate, ethyl propanoate, methyl butanoate, ethyl butanoate and the like.

An "ether" is an organic compound containing an oxygen atom —O— bonded to two other carbon atoms. "$C_2$-$C_6$ ethers" include diethyl ether, diisopropyl ether, methyl t-butyl ether, glyme, diglyme, tetrahydrofuran, 2-methyltetrahydrofuran, 1, 4-dioxane, dibutyl ether, dimethylfuran, diethylene glycol monomethyl ether, diethylene glycol monoethyl ether, anisole and the like.

A "halogenated hydrocarbon" is an organic compound containing a carbon bound to a halogen. Halogenated hydrocarbons include dichloromethane, 1,2-dichloroethane, trichloroethylene, perchloroethylene, 1,1,1-trichloroethane, 1,1,2-trichloroethane, chloroform, carbon tetrachloride and the like.

A "ketone" is an organic compound containing a carbonyl group —(C═O)— bonded to two other carbon atoms. "$C_3$-$C_6$ ketones" include acetone, ethyl methyl ketone, diethyl ketone, methyl isobutyl ketone, ketones and the like.

A "nitrile" is an organic compound containing a cyano —(C≡N) bonded to another carbon atom. "$C_2$-$C_6$ Nitriles" include acetonitrile, propionitrile, butanenitrile and the like.

A "polar aprotic solvents" include N, N-dimethylformamide, N, N-dimethylacetamide, dimethylsulfoxide, sulfolane, N-methylpyrrolidone and the like;

Certain specific aspects and embodiments of the present application will be explained in greater detail with reference to the following examples, which are provided only for purposes of illustration and should not be construed as limiting the scope of the application in any manner. Reasonable variations of the described procedures are intended to be within the scope of the present application. While particular aspects of the present application have been illustrated and described, it would be obvious to those skilled in the art that various other changes and modifications can be made without departing from the spirit and scope of the invention. It is therefore intended to cover in the appended claims all such changes and modifications that are within the scope of this application.

EXAMPLES

Example 1

Preparation of 1-((3aR,5R,6S,6aR)-6-(benzyloxy)-2,2-dimethyltetrahydrofuro[2,3-d][1,3]dioxol-5-yl)-3-hydroxypropan-2-one Acetic acid (13.2 mL) was added to the reaction mass containing (3aR,5R,6S,6aR)-5-allyl-6-(benzyloxy)-2,2-dimethyltetrahydrofuro[2,3-d][1,3]dioxole (10.2 g), acetone (306 mL) and water (62 mL) at 0° C. Solution containing potassium permanganate (11 g) in acetone (102 mL) and water (40 mL) was slowly added to the reaction mass at 0° C. and the resultant reaction mixture was stirred at 0° C. for 3 hours. Ethanol was added to the reaction mass at 5° C., filtered through the Celite bed and washed with ethyl acetate (60 mL). Filtrate concentrated under reduced pressure. The resultant filtrate was extracted with ethyl acetate (2×70 mL), the combined organic layer was washed with saturated sodium bicarbonate solution (3×100 mL), brine solution (1×50 mL) and dried using sodium sulfate (50 g). The resultant organic layer concentrated in vacuo and purified using column chromatography to afford the title compound (5.7 g).

Example 2

Preparation of 3-((3aR,5R,6S,6aR)-6-(benzyloxy)-2,2-dimethyltetrahydrofuro[2,3-d][1,3]dioxol-5-yl)propane-1,2-diol Sodium borohydride (0.98 g) was added to the solution of 1-((3aR,5R,6S,6aR)-6-(benzyloxy)-2,2-dimethyltetrahydrofuro[2,3-d][1,3]dioxol-5-yl)-3-hydroxypropan-2-one (5.6 g) in THF (56 mL) at −78° C. and the resultant reaction mixture was stirred at −78° C. for 4 hours. Reaction mixture was quenched with saturated $NH_4Cl$ solution (28 mL) at −50° C. and allowed to warm to room temperature for 30 minutes. Reaction mixture was extracted with ethyl acetate (2×42 mL) and the combined organic layers were washed with brine solution (1×28 mL), dried over anhydrous Na2SO4 and concentrated in vacuo to afford the title compound (5.5 g; α-isomer-28.34% and β-isomer-68.68% by HPLC).

Example 3

Preparation of 3-((3aR,5R,6S,6aR)-6-(benzyloxy)-2,2-dimethyltetrahydrofuro[2,3-d][1,3]dioxol-5-yl)propane-1,2-diol (+) DIP-Cl (0.506 g, 1.6 M in Hexane) was added to a solution of 1-((3aR,5R,6S,6aR)-6-(benzyloxy)-2,2-dimethyltetrahydrofuro[2,3-d][1,3]dioxol-5-yl)-3-hydroxypropan-2-one (0.35 g) in THF (8 mL) at 0° C. and the resultant reaction mixture was stirred at 30° C. for 24 hours. 10% NaOH (8 mL) and 20% $H_2O_2$ (8 mL) was added to the reaction mixture at 30° C. and stirred for 24 hours. Reaction mixture was extracted with ethyl acetate (3×10 mL), the combined organic layers were washed with brine solution (1×10 mL) and dried over $Na_2SO4$. The resultant organic layer concentrated in vacuo and purified using column chromatography to afford the title compound (0.24 g; purity by HPLC: 94.87%/β-isomer and 5.13% α-isomer).

Example 4

Preparation of (S)-3-((3aR,5R,6S,6aR)-6-(benzyloxy)-2,2-dimethyltetrahydrofuro[2,3-d][1,3]dioxol-5-yl)propane-1,2-diol A buffer cocktail mixture consisting of KRED-101 (44 mg), NAD (20 mg), CDX-901 (7.5 mg) and D-glucose (1.2 g) dissolved in 50 mM potassium phosphate buffer, pH 8 (20 mL) was prepared. The resultant buffer cocktail mix was added to the solution of (3aR,5R,6S,6aR)-5-allyl-6-(benzyloxy)-2,2-dimethyltetrahydrofuro[2,3-d][1,3]dioxole (1.2 g 50 wt %) in toluene. The reaction mixture was continuously stirred at 25° C. and pH was maintained at 7 by periodic additions of 10 wt % aqueous potassium carbonate solution via an auto-titrator for 19.5 hours. Reaction mixture was extracted with ethyl acetate (2×20 mL). The organic extracts were combined, dried over magnesium sulfate and solvent was removed under reduced pressure to afford title compound (Yield: 549 mg; de (diasteromeric excess) by HPLC=99.7%).

Example 5

Preparation of (S)-3-((3aR,5R,6S,6aR)-6-(benzyloxy)-2,2-dimethyltetrahydrofuro[2,3-d][1,3]dioxol-5-yl)propane-1,2-diol A buffer cocktail mixture consisting of CRED A631 (10 mg), NAD (20 mg), CDX-901 (8 mg) and D-glucose (1 g) dissolved in 50 Mm potassium phosphate buffer, pH 8 (20 ml) was prepared. The buffer cocktail mixture was added to the (3aR,5R,6S,6aR)-5-allyl-6-(benzyloxy)-2,2-dimethyltetrahydrofuro[2,3-d][1,3]dioxole in toluene (1.2 g of a 50 wt % solution), resultant reaction mixture was stirred at 25° C. for 24 hours and pH was maintained at 7.5 by periodic additions of 10 wt % aqueous potassium carbonate solution. Reaction mixture was extracted with ethyl acetate (2×20 mL), the combined organic extracts were dried over magnesium sulfate and solvent was removed under reduced pressure to afford title compound.

Example 6

Preparation of (2R,4R)-4-((tert-butyldimethylsilyl)oxy)-6-((2S,5S)-5-(3-((tert-butyldimethylsilyl)oxy)propyl)-3-methylenetetrahydrofuran-2-yl)-2-methyl hexanal Preparation of Borane Ammonia Complex Solution/Suspension:

Borane ammonia complex (82 mg, 2.66 mmol) was added under a nitrogen atmosphere in a round-bottomed flask. This was then inerted via three evacuation/nitrogen re-fill cycles, tetrahydrofuran (1 mL) was charged under nitrogen and the suspension was maintained under a nitrogen atmosphere at 27° C.

n-Butyllithium (1.6 mL of a 1.6M solution in hexanes) was dropwise added to the solution containing tetrahydrofuran (1.5 mL) and diisopropylamine (373 µl) at −75° C. and the resultant solution was stirred at −75° C. for 5 minutes, slowly warmed to 3° C. and stirred at 3° C. for 10 minutes. Borane ammonia suspension was added dropwise at 3° C. and stirred at 3° C. for 10 minutes. The solution was warmed to 27° C., stirred at 27° C. for 10 minutes and then cooled to 3° C. A solution of (2R,4R)-4-((tert-butyldimethylsilyl)oxy)-N-((1R,2R)-1-((tert-butyldimethylsilyl)oxy)-1-phenylpropan-2-yl)-6-((2S,5S)-5-(3-((tert-butyldimethylsilyl)oxy)propyl)-3-methylenetetrahydrofuran-2-yl)-N,2-dimethylhexanamide (270 mg) in tetrahydrofuran (2.5 mL) was added drop-wise under nitrogen atmosphere at 3° C. and the resultant reaction mixture was stirred for 17 hours at 27° C. MTBE (5 mL) was added under nitrogen followed by 1M hydrochloric acid (9 mL) and further MTBE (5 mL). The biphasic mixture was stirred for 1 hour and the phases separated. The aqueous phase was extracted with MTBE (10 mL). The combined organic extracts were washed with 1 M hydrochloric acid (3×5 mL), 1M sodium hydroxide (2×5 mL), brine (10 mL), dried over $MgSO_4$ and concentration in vacuo. The obtained crude alcohol compound was purified using flash column chromatography (123 mg, 71%).

The alcohol compound (60 mg) in a round-bottomed flask was inerted via three vacuum/nitrogen refill cycles and then charged with dichloromethane (1 mL). DMSO (170 µl) and trimethylamine (170 µl) was added and the resultant solution was cooled to 3° C. Pyridine-sulfur trioxide complex (76 mg) was added to the reaction mass at 3° C. and stirred for 19 hours whilst warming to 27° C. Saturated sodium bicarbonate solution (1 mL) and water (1 mL) were added followed by MTBE (10 mL). The phases were separated and the organic phase was washed with water (5 mL) and then brine (10 mL). The combined aqueous phases were extracted with MTBE (8 mL) and the combined organic phases were dried over $Na_2SO_4$ and concentrated in vacuo. The obtained crude compound was purified using flash column chromatography to afford title compound as colourless oil (45 mg, 75%) along with recovered alcohol compound (9 mg, 15%).

Example 7

Preparation of tert-butyl(3-((2S,5S)-5-((3R,5R)-3-((tert-butyldimethylsilyl)oxy)-5-methylhept-6-yn-1-yl)-4-methylenetetrahydrofuran-2-yl)propoxy)dimethylsilane (2R,4R)-4-((tert-butyldimethylsilyl)oxy)-6-((2S,5S)-5-(3-((tert-butyldimethylsilyl) oxy)propyl)-3-methylenetetrahydrofuran-2-yl)-2-methyl hexanal (43 mg) in a round-bottomed flask was inerted via nitrogen purge. Methanol (0.5 mL) was added and the solution was transferred under nitrogen to the reaction flask. Methanol (0.5 mL) was added under nitrogen atmosphere. Dimethyl (1-diazo-2-oxopropyl) phosphonate (500 mg of a 10% solution in acetonitrile) followed by potassium carbonate (27 mg, 0.20 mmol) was added to the reaction mass under a flow of nitrogen and the resultant reaction mixture was stirred for 19 hours. MTBE (15 mL) was added to the reaction mixture, washed with saturated sodium bicarbonate solution (5 mL) and brine (5 mL). The organic extract was dried over $MgSO_4$ and concentrated in vacuo to provide the title compound (39 mg, 92%).

Example 8

Preparation of 3-((2S,5S)-5-((3R,5R)-6-iodo-5-methyl-3-(((2,4,6-triisopropylphenyl)sulfonyl)oxy)hept-6-en-1-yl)-4-methylenetetrahydrofuran-2-yl) propyl pivalate N,N-dimethylpyridin-4-amine (0.947 g) was added to the solution containing 3-((2S,5S)-5-((3R,5R)-3-hydroxy-6-iodo-5-methylhept-6-en-1-yl)-4-methylenetetrahydro furan-2-yl)propyl pivalate (1.03 g) and dichloromethane (15.45 mL) at 5° C. Triethylamine (0.545 g) was added to the reaction mass at 5° C. 2,4,6-triisopropylbenzene-1-sulfonyl chloride (1.956 g) was added to the reaction mass at 5° C. and the resultant reaction mass was stirred at 28° C. for 16 hours. Water (5.15 mL) was added to the reaction mass at 28° C. and stirred at same temperature for 10 minutes. The phases were separated, organic phase was washed with saturated sodium bicarbonate solution (10.3 mL) and then saturated sodium chloride solution (5.15 mL) and the organic phase was concentrated in vacuo. Chased with heptane (5.15 mL). Heptane (10.m mL) was added and stirred for 10 minutes. Acetonitrile (10.3 mL) was slowly added and stirred for 5 minutes. Water (10.3 mL) was added and stirred for 5 minutes. The phases were separated, aqueous phase was extracted with heptane (5.15 mL) and the combined organic phase was washed with saturated sodium chloride solution (5.15 mL). The organic extract was dried over $Na_2SO_4$ and concentrated in vacuo to provide the title compound (1.46 g, 91%).

Example 9

Preparation of 3-((2S,5S)-5-((3R,5R,7R)-8-((2S,3S,4R,5R)-5-(((S)-2,2-dimethyl-1,3-dioxolan-4-yl)methyl)-4-methoxy-3-((phenylsulfonyl) methyl) tetrahydrofuran-2-yl)-7-hydroxy-5-methyl-6-methylene-3-(((2,4,6-triiso propylphenyl)sulfonyl)oxy)octyl)-4-methylenetetrahydrofuran-2-yl)propyl pivalate Chromium (II) chloride (0.924 g) was added to the reaction mixture containing (S)-N-(2-(4-isopropyl-4,5-dihydrooxazol-2-yl)-6-methylphenyl)methanesulfonamide (2.43 g) and anhydrous tetrahydrofuran (25 mL) at 28° C. in glove box. Triethylamine (0.768 g) was added dropwise to the reaction mass at 32° C. and stirred at 31-32° C. for 3 hours 30 minutes. Nickel (II) chloride (0.025 g) was added at 31° C. Solution containing 2-((2S,3S,4R,5R)-5-(((S)-2,2-dimethyl-1,3-dioxolan-4-yl)methyl)-4-methoxy-3-((phenyl sulfonyl)methyl)tetrahydrofuran-2-yl)acetaldehyde (0.67 g), 3-((2S,5S)-5-((3R,5R)-6-iodo-5-methyl-3-(((2,4,6-triisopropylphenyl)sulfonyl)oxy)hept-6-en-1-yl)-4-ethylene tetrahydrofuran-2-yl)propyl pivalate (1.573 g) and tetrahydrofuran (15 mL) was added slowly to the reaction mixture at 31° C. and stirred at 31° C. for 16 hours. Ethylenediamine (1.3 g) was slowly added to the reaction mass at −4° C. and stirred at 0-2° C. for 1 hour. Water (10 mL) was added slowly at 10° C. and n-heptane (20 mL) followed by MTBE (20 mL) was added slowly to the reaction mass at 16° C. and stirred for 20 minutes. The phases were separated, aqueous phase was extracted with MTBE (2×30 mL) and the combined organic phase was washed with solution of sodium bicarbonate (1.0 g) and sodium chloride (3 g) in water (12 mL). The organic extract was dried over anhydrous $Na_2SO_4$ and concentrated in vacuo. The resultant crude compound was chased with tetrahydrofuran (2×30 mL) and used for cyclization reaction (Next step).

Example 10

Preparation of 3-((2S,5S)-5-(2-((2S,4R,6R)-6-(((2S,3S,4R,5R)-5-(((S)-2,2-dimethyl-1,3-dioxolan-4-yl)methyl)-4-methoxy-3-(phenylsulfonyl)methyl) tetrahydrofuran-2-yl)methyl)-4-methyl-5-methylenetetrahydro-2H-pyran-2-yl) ethyl)-4-methylenetetrahydrofuran-2-yl)propyl pivalate KHMDS (0.5 M in toluene) (20.5 mL) was added slowly to the reaction mass containing 3-((2S,5S)-5-((3R,5R,7R)-8-((2S,3S,4R,5R)-5-(((S)-2,2-dimethyl-1,3-dioxolan-4-yl)methyl)-4-methoxy-3-((phenylsulfonyl) methyl)tetrahydrofuran-2-yl)-7-hydroxy-5-methyl-6-methylene-3-(((2,4,6-triisopropylphenyl)sulfonyl)oxy)octyl)-4-methylenetetrahydrofuran-2-yl)propyl pivalate (1.675 g) and tetrahydrofuran (40 mL) at −20° C. and stirred at −20° C. for 1 hour. Reaction mass was cannulated to solution of ammonium chloride (5.0 g) in water (50 mL) at −8° C., MTBE (50 mL) was added and warmed to ambient temperature over 30 minutes. The phases were separated, aqueous phase was extracted with MTBE (2×30 mL) and the combined organic phase was washed with brine solution (30 mL). The organic extract was dried over anhydrous $Na_2SO_4$ and concentrated in vacuo. The obtained crude compound was subjected to Combiflash purification to afford title compound (0.52 g, 95.02% purity by HPLC).

The invention claimed is:

1. A process for preparation of compound of formula IX,

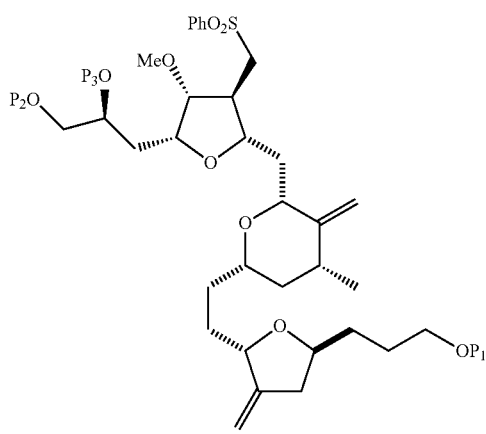

IX wherein $P_1$, $P_2$ and $P_3$ is an alcohol protecting group selected from acetyl, benzoyl, benzyl, β-methoxyethoxymethyl ether, methoxymethyl ether, dimethoxytrityl, p-methoxybenzyl ether, methylthiomethyl ether, allyl ether, t-butyl ether, pivaloyl, trityl, silyl ether, tetrahydropyranyl (THP), methyl ether, ethoxyethyl ether (EE) and $P_2$ and $P_3$ together protected by forming acetonide (cyclic ketal); said process comprising:

(a) reacting compound of formula Va with compound of formula X to provide compound of formula XI; and

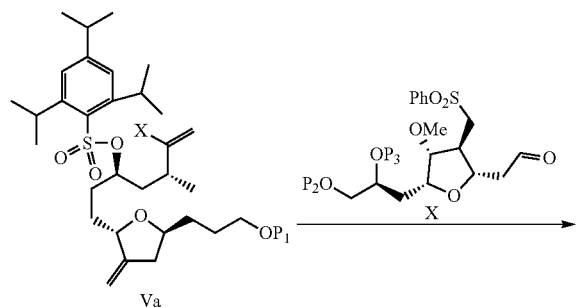

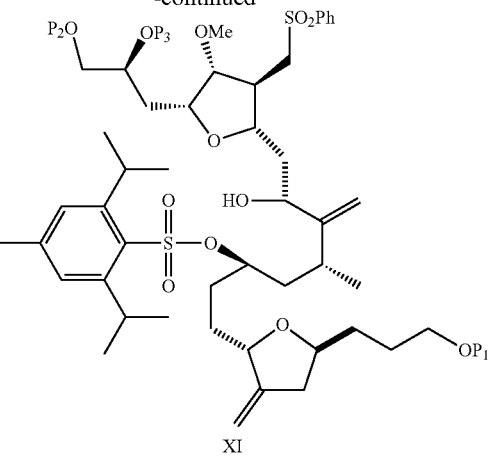

XI wherein X is a halogen selected from Cl, Br or I;

(b) treating compound of formula XI with a suitable reagent to provide compound of formula IX.

2. The process according to claim 1, wherein the compound of formula Va is

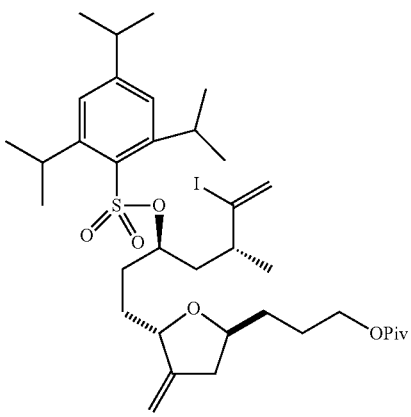

wherein Piv is Pivaloyl.

3. A process for preparation of eribulin or a pharmaceutically acceptable salt thereof, said process comprising producing the eribulin or a pharmaceutically acceptable salt thereof from the compound of claim 1.

* * * * *